United States Patent [19]

Fremont

[11] 4,143,231

[45] Mar. 6, 1979

[54] BUTINEDIOL USING CATALYST PREPARED FROM SYNTHETIC MALACHITE

[75] Inventor: Joseph M. Fremont, Glen Mills, Pa.

[73] Assignee: E. I. Du Pont de Nemours and Company, Wilmington, Del.

[21] Appl. No.: 870,024

[22] Filed: Jan. 16, 1978

Related U.S. Application Data

[60] Division of Ser. No. 794,674, May 6, 1977, Pat. No. 4,107,082, which is a continuation of Ser. No. 687,179, May 17, 1976, abandoned, which is a continuation-in-part of Ser. No. 445,476, Feb. 25, 1974, abandoned.

[51] Int. Cl.$^2$ ............................................... C07C 33/04
[52] U.S. Cl. .................................................... 568/855
[58] Field of Search ........................................ 568/855

[56] References Cited

U.S. PATENT DOCUMENTS

| 2,300,969 | 11/1942 | Reppe et al. | 568/855 |
| 3,650,985 | 3/1972 | Kirchner | 568/855 |

*Primary Examiner*—Joseph E. Evans

[57] ABSTRACT

Synthetic malachite of desirable particle size and distribution is coprecipitated with small amounts of uniformly dispersed bismuth. After nucleation, the crystals are grown at elevated temperatures. The malachite can be converted into a cuprous acetylide complex useful as an ethynylation catalyst.

1 Claim, No Drawings

BUTINEDIOL USING CATALYST PREPARED FROM SYNTHETIC MALACHITE

CROSS REFERENCE TO RELATED APPLICATION

This application is a divisional of application Ser. No. 794,674, filed May 6, 1977 now U.S. Pat. No. 4,107,082; which in turn is a continuation of application Ser. No. 687,179, filed May 17, 1976; now abandoned, which is a continuation-in-part of application Ser. No. 445,476, filed Feb. 25, 1974, now abandoned.

BACKGROUND OF THE INVENTION

This invention relates to a process for coprecipitating malachite with bismuth, to a process of making a cuprous acetylide complex ethynylation catalyst starting with such coprecipitation, and to the complex produced.

In the production of 1,4-butynediol by the reaction of acetylene with formaldehyde in the presence of a cuprous acetylide complex catalyst, it is known to be desirable to inhibit the formation of cuprene, polymerized acetylene, by the use of inhibitors such as bismuth oxide. U.S. Pat. No. 2,300,969—Reppe et al. (1942) discusses the use of several such inhibitors in the formation and use of such catalysts at elevated pressures such as about 20 atmospheres. U.S. Pat. No. 3,650,985—Kirchner (1972) mentions the utility of bismuth oxide as a cuprene inhibitor in cupric acetylide catalyst made and used at low partial pressures of acetylene, below 2 atmospheres. Neither of these patents indicates how the bismuth values can be incorporated uniformly into the catalyst itself.

It has been found that in the production of the low pressure catalysts according to U.S. Pat. No. 3,650,985, if bismuth oxycarbonate is added separately to preformed malachite, it will separate in the catalyst which is eventually prepared, leading to unsatisfactory results. Thus, it is desirable to have a satisfactory method of coprecipitating bismuth in the basic cupric carbonate or malachite which is the catalyst precursor.

Basic copper carbonate, known as malachite, $Cu_2(OH)_2CO_3$, is normally prepared by either of two precipitation techniques. In the first, a solution of a copper salt such as copper nitrate or chloride is neutralized to a pH of 7.0 with sodium or potassium carbonate or bicarbonate. Initially, hydrated copper carbonate, amorphous $CuCO_3 \cdot x(H_2O)$, precipitates in the form of a thick gelatinous material which, on heating, slowly converts to malachite with the elimination of $CO_2$. Precipitates of crystals of malachite made by this technique generally comprise irregularly shaped particles ranging in size from less than 1 micron ($\mu$) to more than $25\mu$ in average particle cross-sectional dimension. If the gel has set up thoroughly, then the irregularity and broad distribution of crystallite size on crystallization seem to be a result of tearing of the gel as it precipitates. The irregularly-shaped crystallites and wide distribution of particle size is rather undesirable for use as a precursor in the production of cuprous acetylide ethynylation catalysts.

Another method for the precipitation of malachite involves feeding simultaneously the copper solution and the carbonate neutralization agent with agitation to maintain a pH in the range of 5 to 8. The hydrated copper carbonate so obtained is also subsequently converted to malachite at ambient temperature or more rapidly as the temperature is increased. This technique produces a more regular crystalline product which consists of agglomerates of individual crystallites of about 2 to $3\mu$ average cross-sectional dimension. The agglomerates range in size up to a maximum of about $30\mu$. As with the first method of adding the carbonate neutralizer to the copper solution, so too with this method of simultaneously feeding them together, an amorphous hydrated copper carbonate is initially formed.

It would be desirable to have a process for the production of basic copper carbonate crystalline particles having bismuth incorporated therein with the particles being of a fairly uniform and relatively large particle size. The uniformity of dispersion of bismuth in the particles is desirable to permit the formation of ethynylation catalyst in which the bismuth values will remain in place and continue to be effective in the prevention of cuprene formation.

SUMMARY OF THE INVENTION

The present invention provides a process for the production of crystalline particles of basic copper carbonate having uniformly dispersed therein bismuth in amounts in the range of 2 to 5 percent by weight based on the amount of copper present. The process comprises three steps. First, hydrated copper carbonate particles are precipiated by the addition to water, preferably simultaneously, of solutions of cupric salts and alkali metal carbonate or bicarbonate to form a reaction mixture. The solutions are in such proportions as to maintain the pH about in the range of 5.0 to 8.0. Then the hydrated copper carbonate is converted to basic copper carbonate in the reaction mixture at a temperature of at least about 60° C. This conversion occurs through the nucleation of crystallites of malachite from the amorphous hydrated copper carbonate. Subsequent additions of copper, bismuth and carbonate precipitate on these converted nuclei as more malachite. The nucleated crystalline particles and agglomerates of such particles are grown while the bismuth is incorporated uniformly into the particles. The reaction mixture is kept at temperatures of at least about 60° C. during the growth. The solutions of cupric salts, bismuth salts and sodium carbonate or bicarbonate are added in such proportions as to maintain the pH about in the range of 5.0 to 8.0 until the average cross-sectional dimension of the agglomerates of crystallites is at least about 10 microns.

The bismuth content herein is expressed in terms of percent by weight based on the amount of copper present. Parts, percentages and proportions herein are by weight except where indicated otherwise.

Although it is necessary to have the bismuth present during the particle growth, it is also desirable and, as a practical matter may be necessary, to have it present also during the precipitation and nucleation steps.

The coprecipitated basic copper carbonate-bismuth particles can be used to make a cuprous acetylide complex useful as an ethynylation catalyst. The basic copper carbonate-bismuth particles are subjected as a slurry in aqueous medium at 50° to 120° C., to the simultaneous action of formaldehyde and acetylene at a partial pressure of not more than 2 atmospheres. The aqueous medium has a pH of 3 to 10 at the initiation of the subjecting. Preferably, the reaction is continued until all of the cupric precursor is converted to the cuprous acetylide complex. It is desirable for the medium in which the subjecting is done to have a pH in the range of 5 to 8 at least initially.

The resulting catalysts made from such precursors are a particulate cuprous acetylide complex which consists essentially of copper, carbon, hydrogen, oxygen and bismuth in proportions corresponding to the general formula $$(CuC_2)_2(CH_2O)_x(C_2H_2)_y(H_2O)_z—Bi$$

wherein, when $w = 4$, $x = 0.24$ to $4.0$, $y = 0.24$ to $2.40$ and $z = 0.67$ to $2.80$, and in which the bismuth is present in an amount of .2 to 5%. The complex particles have a total surface area of at least 5 m.$^2$/g., and the average particle cross-sectional dimension is at least $10\mu$.

Preferably, the particulate complex has a total surface area of 15 to 75 m.$^2$/g., the average particle cross-sectional dimension being in the range of 10 to $40\mu$, containing 20 to 66% copper, 2 to 12.5 carbon atoms per copper atom, 0.2 to 2 hydrogen atoms per carbon atom, 0.1 to 1 oxygen atom per carbon atom, and 3 to 4% bismuth.

DETAILED DESCRIPTION

In contrast to the basic copper carbonate crystal production methods of the prior art, the method of the present invention utilizes a rapid precipitation of hydrated copper carbonate followed by nucleation and conversion of the hydrated copper carbonate to basic copper carbonate (malachite). The nucleation and conversion are encouraged by an elevated temperature, such as over 60° C. The larger proportion of the reactants for forming the basic copper carbonate, such as at least two-thirds of the copper, is not added to the reaction mixture until after the conversion to basic copper carbonate. At this time, the copper salts, neutralizing chemicals and bismuth combine readily to produce a uniform dispersion of bismuth in basic copper carbonate crystalline particles of rather uniform and large particle size. This crystal growth avoids the initial formation of further gelatinous hydrated copper carbonate.

If the entire production of the basic copper carbonate crystals is done at elevated temperatures such as over 60° C., including precipitation, nucleation and growth, the hydrated copper cabonate is not present for much time at all. Nucleation and conversion occur rapidly, and growth of the initial nuclei is the main phenomenon occurring. Thus, operating all steps of the production at elevated temperature leads to the production of smaller numbers of larger particles. Actually, each of the steps will take place at lower temperatures such as room temperature, about 23° C. Many nuclei would form and convert to malachite before crystal growth depleted the concentration of reactants, leading to the prevalence of smaller particle sizes. Also, with malachite production at lower temperatures, the bismuth values are not uniformly included in the basic copper carbonate made this way but tend to segregate either during formation of the carbonate or later during use of the carbonate to form cuprous acetylide complexes for use as ethynylation catalysts. Thus, it is important to use the procedure of the invention to form the basic copper carbonate-bismuth coprecipitates to be used in making the ethynylation catalysts.

For the production of smaller-sized crystallites and agglomerates, the nucleation can be conducted at a lower temperature followed by an increase in temperature to above 60° C. for relatively rapid conversion and growth and uniform dispersion of the bismuth. For the production of larger-sized crystallites and agglomerates, the nucleation also would be conducted at a higher temperature such as above 60° C.

If the pH is raised at least 1.0 unit between the nucleation step and the growth step, this can lead to even greater uniformity in particle size. Crystal growth occurs optimally in a band representing super-saturation on a plot of solubility versus temperature. The super-saturation band is wider for these products at higher pH values. Therefore, higher pH within limits will lead to more deposition on existing nuclei and less formation of new small nuclei if the reaction continues to be conducted in the super-saturation band.

The conversion of the hydrated copper carbonate to malachite as the malachite nucleates can be readily observed. Hydrated copper carbonate is blue and it tends to be a structureless gelatinous mixture. The malachite is green and crystalline.

If sodium carbonate is added to a copper nitrate solution having a pH of 3, as the pH rises to 4½ the reaction product sets up as a thick gel. Further pH rise and agitation break up the gel, tearing as it converts to malachite to form very irregular particles related to the size of the torn gel. Above a pH of about 8.0, and at elevated temperatures the amorphous copper carbonate hydrate begins to convert to copper oxide which is undesirable. Below a pH of 5.0, the gel formation becomes troublesome.

During the catalyst production, sodium iodide can be added separately. This produces some bismuth oxyiodide in the catalyst which acts as a further inhibitor for cuprene formation.

The catalyst is desirably about 15 to $20\mu$ agglomerate size. Larger particles have advantages over smaller particles including more rapid filtration and drying, lack of dust formation and lack of band formation on settling. Fifty $\mu$ agglomerate size is larger than desirable due to decreased activity of the catalyst. Catalyst particles that are too small lead to filtering difficulties. The size of the agglomerates can be readily controlled by adjusting the temperature and pH of the steps of the production of the basic copper carbonate.

During the ethynylation reaction, acetylene inhibits the valence change of cuprous copper in the catalyst to elemental copper or cupric copper. This is desirable, because elemental copper is a catalyst for the polymerization of acetylene to cuprene. Cuprene is quite undesirable in these reactions because it tends to clog filters and cannot be readily removed. During some upset conditions in production operations, the flow of acetylene into the reactor is shut off due to emergency or sudden loss of supply. Bismuth, such as in the form of oxycarbonate uniformly incorporated in the catalyst, aids in protecting the catalyst from such degradation even while hot and in the absence of acetylene.

Above 4 or 5% bismuth, a second phase tends to separate from the catalyst after some weeks of operation in the ethynylation catalyst. This manifests itself in the formation of fine particles which cause filter difficulties. Also, such separation would tend to degrade the operation of the bismuth in the catalyst.

With a solubility level in the ethynylation reaction media of about 0.5 ppm, bismuth can be digested out of the catalyst. This is more of a problem if the bismuth content of the catalyst is over about 3%, but it is not a serious problem until above about 5% bismuth content.

In preferred techniques according to the invention, bismuth nitrate in the desired concentration is dissolved in the copper nitrate solution which is then fed with sodium carbonate to a crystalizer, preferably simultaneously. In batch operations one could be fed into the other, and for semicontinuous operation an excess of one could be fed to a heel containing the other. The pH is maintained between 6 and 7, and the temperature is in the 60°–80° C. range during crystal growth. For larger crystals, the temperature is also in that region initially for the precipitation and nucleation. In the resulting malachite, the bismuth is effectively coprecipitated and uniformly dispersed. When such bismuth-containing malachite is utilized to form a cuprous acetylide complex ethynylation catalyst for butynediol synthesis, a substantial improvement in catalyst filterability and stability results.

Bismuth-containing malachite has been prepared according to the invention using early nucleation techniques but with bismuth concentrations of 1, 2, 3, 4, 8, 10 and 15%. The resulting malachite was then used to prepare the ethynylation catalysts. Catalysts thus obtained were then subjected to extended life tests to determine the improved stability and operability as indicated by the absence of cuprene formation. For comparative purposes, catalysts were also made with a commercial grade of malachite. Life tests were run for a period of about 100 hours or more at which time the catalyst was removed and examined for the presence of cuprene. Cuprene is readily detected visibly by its copper color, and it generally floats to the surface in the formaldehyde-water solutions used for the production of butynediol. Excess bismuth salts can also digest out of the catalyst and form residues of other colors.

Life test results showed that catalysts produced from bismuth-free malachite precursors produced substantial amounts of cuprene during the 100-hour life test. Even more cuprene was produced when the catalyst was kept hot in the absence of acetylene, simulating the sudden loss of acetylene in a butynediol manufacturing operation. Furthermore, when 5% bismuth in the form of bismuth subcarbonate was mixed with bismuth-free malachite and the mixture was subsequently converted to catalyst, substantial cuprene formation was still evident when the catalyst was evaluated. A trace of cuprene was also noticed with the catalyst containing 1% bismuth, but the catalysts made from malachite coprecipitated with higher amounts of bismuth remained cuprene free. With 2% or more bismuth coprecipitated in the malachite, the resulting catalyst could be held in an acetylene-free environment for short periods such as up to about ½ hour at elevated temperatures such as between 70° and 95° C. without degradation that causes excessive cuprene formation, which would end the useful life of the catalyst.

At bismuth loadings of 5% and higher, some bismuth separation from the catalyst results after extended use. Thus it appears that bismuth concentrations above 4% are less desirable, and concentrations in the 3 to 4% range appear optimum for overall performance. One preferred catalyst with a 3% bismuth content was used in the production of butynediol for 20 days without evidence of degradation or cuprene formation. Furthermore, the relatively large and uniform particle sizes of catalysts obtained according to the present invention result in easier filtration. In butynediol preparation methods wherein the catalyst system operates as a slurry and the product is removed through a candle filter technique, the larger particle size is able to permit increased filtration rates.

EXAMPLE 1

Malachite — 4% Bi Starting Cold

Crystalline particulate synthetic malachite containing 4% bismuth was prepared in accordance with the invention as follows.

Into a reaction vessel containing 300 cc. of water are simultaneously added two streams. One stream is a saturated solution of $Na_2CO_3$ in water and the other is a water solution containing 100 g. $Cu(NO_3)_2.3H_2O$, 2.32 g. $Bi(NO_3)_3.5H_2O$, 10 cc. $HNO_3$ and 90 cc. of $H_2O$. The streams are added at rates such as to keep the pH in the precipitation vessel continuously at about 6.5, and heat is gradually applied from the beginning to commence the precipitation. The following table shows the rate of solution addition measured in terms of the copper nitrate solution still to be added, time since commencing addition and the temperature of the reaction mixture.

TABLE I

MALACHITE PRODUCTION

| Time Minutes | Temperature (° C.) | Solution to be Added (cc. CuNO₃) |
|---|---|---|
| 0 | 35 | 150 |
| 10 (nucleation) | 70 | 125 |
| 35 | | 22 |
| 72 | 75 | 0 |

The reaction product was allowed to digest until it reached a pH of 8.0 and then was filtered and dried. The particles had an average cross-sectional dimension of 15–20μ. The product contained 4% bismuth uniformly dispersed through the crystalline particles.

It is desirable to add only about ¼ to ⅓ of the reactants until nucleation and conversion occur, which may happen simultaneously, and then to add the remaining reactants after nucleation to grow the bismuth-containing-malachite crystals.

EXAMPLE 2

Malachite — 3% Bi Starting Cold

Crystalline particulate synthetic malachite containing 3% bismuth was prepared in accordance with Example 1, but using 1.74 g. $Bi(NO_3)_3.5H_2O$. The following table shows data analogous to that of Example 1, and also gives the pH at several times during the reaction.

TABLE II

MALACHITE PRODUCTION

| Time Minutes | Temperature (° C.) | Solution to be Added (cc. CuNO₃) | pH |
|---|---|---|---|
| 0 | 85 | 140 | 6.5 |
| 15 | 75 | 125 | 6.5 (nucleation) |
| 27 | 75 | 100 | 6.5 (all material converted to malachite, change pH to 7.5) |
| 35 | 75 | 50 | 7.4 |
| 41 | 75 | 25 | 7.4 |
| 50 | 75 | 0 | 6.7 |

The nucleation was accomplished at a pH of 6.5, and then the pH was increased to 7.5 to grow the crystals. The crystallizing was finished at a pH of 6.8 to insolubilize all the malachite. The product was then digested to a pH of 8.0, washed, filtered and dried. The resulting product had particles of 15 to 25 microns cross-sectional dimension with good dispersion of bismuth at the 3% level.

EXAMPLE 3

Catalyst Preparation

In a typical catalyst preparation 45 g. of malachite containing 3% bismuth and 25 g. Cu is charged to a glass vessel with jacket heating along with 600 g. of 37% formaldehyde and 2 g. of $CaCO_3$ for neutralizing the formic acid generated. A $N_2$-diluted $C_2H_2$ stream is passed through the vessel using a sintered glass frit for gas distribution. Temperature is controlled between 70° and 80° C. and pressure at 4 to 5 psig. As the malachite is converted to copper acetylide, $CO_2$ is eliminated and the system is thus provided with a vent to effect $CO_2$ removal. The system is also equipped with a small recycle gas pump so that unreacted $C_2H_2$ is recycled, and makeup $C_2H_2$ and $N_2$ are added to maintain the pressure. The $C_2H_2$ concentration, as measured by gas chromatography in the off gas, is generally maintained in the 2 to 5% by volume range to achieve the most active catalyst. After all $CO_2$ is eliminated the reactor is cooled, the contents are removed and the catalyst is washed with water to eliminate product butynediol and unreacted formaldehyde. The catalyst thus obtained is stored under water until it is subjected to evaluation with respect to stability and long term activity.

EXAMPLE 4

Catalyst Evaluation Life Test

For evaluation, the catalyst derived from a 45 g. malachite charge is charged to a jacketted vessel with 600 cc. of 15% formaldehyde solution. Acetylene gas is passed through a sintered glass frit to achieve the necessary distribution and mass transfer. Reactor temperature is increased to 90° C. and after 8 hours to 95° C. Acetylene is fed continuously as is a 37% formaldehyde solution to maintain a steady state 10% formaldehyde concentration. Product is continuously withdrawn through a sintered glass filter so that catalyst remains in the reactor. Sodium bicarbonate solution is added continuously to maintain pH in the 6.0 to 6.2 region as measured by an in-reactor pH probe. Total reactor pressure is maintained at 5 psig. Activity is measured as weight units of $C_2H_2$ consumed/hour/weight unit of copper in the reactor and is calculated continuously from the rate of formaldehyde consumption. A life test runs for approximately 100 hours or longer after which the system is cooled, the catalyst withdrawn, filtered and washed free from reactants and product and examined for cuprene content. Cuprene is readily detected by its characteristic copper color and tends to float on the surface of the water layer under which the evaluated catalyst is stored.

Table III below summarizes the results of life tests with cuprous acetylide catalysts of the invention. When more than 5% bismuth was used, various colored materials were deposited on the catalyst. Bismuth salts separate as a result of bismuth digesting out of the catalyst. Above 1% bismuth, cuprene was not detected except in the cases in which the bismuth was not coprecipitated with the malachite at temperatures of the invention, tests 11 and 12. Catalysts containing 2, 5 and 15% bismuth were exposed to elevated temperatures in the absence of acetylene without deleterious subsequent formation of cuprene.

TABLE III
CATALYSIS WITH BISMUTH

| Test | % Bi | Time (hrs.) | Time Yield ($C_2H_2$/Cu-hr.) | Cuprene | Remarks |
|---|---|---|---|---|---|
| 1 | 15 | 210 | 0.75 | — | Bi salt separated |
| 2 | 15 | 175 | 0.63 | — | Bi salt separated |
| 3 | 10 | 207 | 0.6 | — | Bi salt separated |
| 4 | 8 | 85 | 0.7 | — | Bi salt separated |
| 5 | 5 | 187 | 0.7-0.6 | none | |
| 6 | 3 | 205 | 0.7 | none | clear |
| 7 | 2 | 99 | 0.56 | none | |
| 8 | 1 | 105 | 0.5 | visible | |
| 9 | 1 | 102 | 0.65 | visible | |
| 10 | 0 | 90 | 0.5 | visible | malachite without Bi |
| 11 | 5 | 100 | 0.5 | extensive | added $(BiO)_2CO_3$ to malachite without coprecipitating |
| 12 | 4 | 90 | 0.75 | visible | precipitated at room temperature (23° C.), Bi separated |

I claim:

1. In the production of 1,4-butynediol by reaction of acetylene and formaldehyde in the presence of a cuprous acetylide catalyst, the improvement comprising use of a catalyst consisting essentially of a particulate cuprous acetylide complex having uniformly dispersed therein bismuth in the amount of 2 to 5 percent by weight based on the amount of copper present and produced by precipitating hydrated copper carbonate particles by the addition to water of solutions of cupric salts and alkali metal carbonate or bicarbonate to form a reaction mixture, said solutions being in such proportions as to maintain the pH about in the range of 5.0 to 8.0, nucleating and converting the hydrated copper carbonate to basic copper carbonate in the reaction mixture at a temperature of at least about 60° C., and growing agglomerates of the nucleated crystalline particles by precipitating basic copper carbonate containing bismuth by the addition to the reaction mixture of solutions of cupric salts, bismuth salts and alkali metal carbonate or bicarbonate in such proportions as to maintain the pH about in the range of 5.0 to 8.0 with the reaction mixture at a temperature of at least about 60° C. until the average cross-sectional dimension of the agglomerates of crystallites is at least about 10 microns, and then subjecting the agglomerated basic copper carbonate as a slurry in aqueous medium at 50° to 120° C., to the simultaneous action of formaldehyde and acetylene at a partial pressure of not more than 2 atmospheres, said aqueous medium having a pH of 3 to 10 at the initiation of said subjecting, and continuing the reaction until said complex is obtained.

* * * * *